United States Patent

Forte et al.

[11] Patent Number: 6,103,895
[45] Date of Patent: Aug. 15, 2000

[54] PREPARATION OF (11β,16β)-21-(ACETYLOXY)-11-HYDROXY-2'-METHYL-5'H-PREGNA-1,4-DIENO[17,16-D]OXAZOLE-3,20-DIONE

[75] Inventors: Luigi Forte; Calogero Cancellieri, both of Brindisi, Italy

[73] Assignee: Gruppo Lepetit S.p.A., Milan, Italy

[21] Appl. No.: 09/077,728

[22] PCT Filed: Dec. 4, 1996

[86] PCT No.: PCT/EP96/05390

§ 371 Date: Jun. 5, 1998

§ 102(e) Date: Jun. 5, 1998

[87] PCT Pub. No.: WO97/21722

PCT Pub. Date: Jun. 19, 1997

[30] Foreign Application Priority Data

Dec. 13, 1995 [DE] Germany .............................. 95119626

[51] Int. Cl.$^7$ ...................................................... C07J 71/00
[52] U.S. Cl. ................................................................ 540/56
[58] Field of Search .................................................. 540/56

[56] References Cited

FOREIGN PATENT DOCUMENTS 0 322 630  7/1989  European Pat. Off. .
250 538  10/1987  Germany .

OTHER PUBLICATIONS

Ed. W. Gerhartz & Y. S. Yamamoto, Ullamann's Encyclopedia of Industrial Chemistry, vol. A1, pp. 65–66, 1985.

*Primary Examiner*—Johm M. Ford
*Assistant Examiner*—Brenda Coleman
*Attorney, Agent, or Firm*—Balarm Gupta

[57] ABSTRACT

A process for preparing the compound (11β,16β)-21-(acetyloxy)-11-hydroxy-2'-methyl-5'H-pregna-1,4-dieno[17,16-d]oxazole-3,20-dione (INN deflazacort) which comprises reacting (11β,16β)-11,21-dihydroxy-2'-methyl-5'H-pregna-1,4-dieno[17,16-d]oxazole-3,20-dione with acetic anhydride in a suitable organic solvent in the presence of a basic catalyst and water.

12 Claims, No Drawings

PREPARATION OF (11β,16β)-21-(ACETYLOXY)-11-HYDROXY-2'-METHYL-5'H-PREGNA-1,4-DIENO[17,16-D]OXAZOLE-3,20-DIONE

This application is a national stage entry under 35 U.S.C. § 371 of an International Application No. PCT/EP96/05390, filed Dec. 4, 1996, which claims the benefit of priority of EP application 95119626.0, filed Dec. 13, 1995.

The present invention refers to a new process for preparing the compound (11β16β)-21-(acetyloxy)-11-hydroxy-2'-methyl-5'H-pregna-1,4-dieno[17,16-d] oxazole-3,20-dione, also known, and hereinafter referred to, with the INN (International Nonproprietary Name) deflazacort. Deflazacort is represented by the following formula I

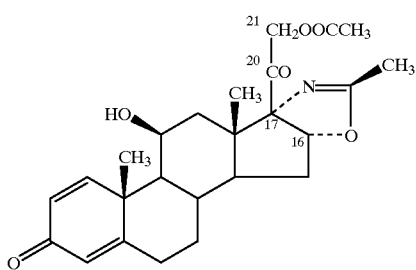

Deflazacort is employed in therapy since some years as a calcium-sparing corticoid agent.

This compound belongs to the more general class of pregneno-oxazolines, for which anti-inflammatory, glucocorticoid and hormone-like pharmacological activities are reported. Examples of compounds of the above class, comprising deflazacort, are disclosed in U.S. Pat. No. 3,413,286, where deflazacort is referred to as 11β-21-dihydroxy-2'-methyl-5'βH-pregna-1,4-dieno[17,16-d]oxazole-3,20-dione 21-acetate.

According to the process disclosed by U.S. Pat. No. 3,413,286, deflazacort is obtained from 5-pregnane-3β-ol-11,20-dione-2'-methyloxazoline by 2,4-dibromination with $Br_2$-dioxane, heating the product in the presence of LiBr-$LiCO_3$ for obtaining the 1,4-diene, and converting this latter into the 21-iodo and then into the desired 21-acetyloxy compound. By hydrolysis of deflazacort, the 11β-21-dihydroxy-2'-methyl-5'βH-pregna-1,4-dieno[17,16-d-]oxazoline-3,20-dione of formula II is obtained:

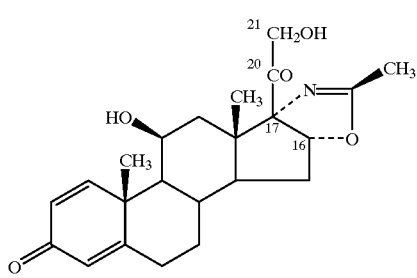

The compound of formula II is preferably obtained according to a fermentation process disclosed in EP-B-322630; in said patent, the compound of formula II is referred to as 11β-21-dihydroxy-2'-methyl-5'βH-pregna-1,4-dieno[17,16-d-]oxazoline-3,20-dione.

The present invention provides a new advantageous single-step process for obtaining deflazacort, by acetylation of the compound of formula II.

More in detail, the process of the present invention comprises reacting the compound of formula II with acetic anhydride in a suitable organic solvent in the presence of a basic catalyst and water.

The starting material of formula II is obtained according to the procedures known in the art, for instance according to the fermentation process disclosed in the above cited EP-B-322630, here incorporated by reference. Said patent discloses a fermentation process for obtaining the compound of formula II, wherein a 2'-methyl-4-pregnen-21-ol-[17α16α-d-]oxazolinyl-3,20-dione is contacted with a sequentially growing mixed culture of a Curvularia strain and an Arthrobacter strain. More in particular, according to a preferred embodiment, the above compound is added to a growing culture of C. lunata NRRL 2380 in a suitable fermentation medium after 12–24 hours from inoculum, and, after 48–72 hours from inoculum, a growing culture of A. simplex ATCC 6946 of 18–36 hours is added to the mixture and further cultivated for 40–55 hours; the fermentation is carried out under submerged conditions, temperature is kept between 27° C. and 32° C. and pH between 6 and 8; the fermentation product of formula II is recovered according to procedures known in the art.

Organic solvents suitable for the process of the present invention are those which are able to at least partially solubilize the starting materials, without negatively affecting the reaction course. Examples of suitable organic solvents are halogenated ($C_1$–$C_4$)hydrocarbons, ($C_1$–$C_4$)alkyl esters of ($C_1$–$C_4$) carboxylic acids, dimethylformamide, acetonitrile, acetone and the like. Preferred solvents are the ($C_1$–$C_4$)alkyl esters of ($C_1$–$C_4$) carboxylic acids, such as methyl, ethyl, propyl, iso-propyl, butyl, 2-methylpropyl or t-butyl formiate; methyl, ethyl, propyl, iso-propyl, butyl, 2-methylpropyl or t-butyl acetate; methyl, ethyl, propyl, iso-propyl, butyl, 2-methylpropyl or t-butyl propionate; methyl, ethyl, propyl, iso-propyl, butyl, 2-methylpropyl or t-butyl butirrate; methyl, ethyl, propyl, iso-propyl, butyl, 2-methylpropyl or t-butyl iso-butirrate. Particularly preferred is ethyl acetate.

The reaction temperature may vary from about −15° C. to 30° C., depending on the other reaction parameters; preferably it is set from −5°C. to 10° C., particularly preferred being about 5° C.

The acetic anhydride is preferably reacted in a molar excess with respect to the stoichometric ratio with the compound of formula II; preferably, the molar ratio between the compound of formula II and acetic anhydride is from about 1.0:1.2 to about 1.0:2, particularly preferred being a molar ratio of about 1.0:1.4.

Basic catalysts useful in the present process are tertiary organic aliphatic or alicyclic amines such as trimethylamine, triethylamine, N-methyl pyrrolidine or heterocyclic bases such as pyridine, 4-(N,N-dimethyl-amino)-pyridine, 4-(N,N-diethylamino)pyridine, collidine, picoline, and the like. Preferably, 4-(N,N-dimethylamino)-pyridine is employed. The catalytic amount will depend from the specific catalyst employed; in general it will be from about 0.05 to about 0.30 times the molar amount of thercompound of formula II. Preferably its molar amount is about 0.05 to 0.10 times the molar amount of the compound of formula II; in particular when the molar ratio between deflazacort alcohol and acetic anhydride is about 1.0:1.4 and 4-(N,N-dimethylamino)-pyridine is the selected catalyst, its molar amount is about 0.06 times the molar amount of the compound of formula II.

In general an amount of water from 3 to 20 times the molar amount of the compound of formula II is present in the reaction mixture, preferably from 5 to 15 times. Under the above preferred conditions, i.e. for a molar ratio of compound of formula II: acetic anhydride: catalyst of about 1.0:1.4 :0.06the molar excess of water with respect to the compound of formula II will be of about 10 times.

The reaction time will vary depending on the above reaction parameters and conditions. As a general indication, the reaction is completed in from 4 to 15 hours. In any case the reaction course can-be easily followed according to the standard techniques known in the art, such as by HPLC or TLC usually by following the formation of the final product deflazacort. Thus, on the basis of the results of these assays, the skilled man is able to evaluate when to stop the reaction for starting up with the recovery of the desired product.

The reaction product is recovered according to the standard procedures known in the art; for instance the reaction mixture is washed with a suitable buffering solution (such as phosphate, carbonate and the like, pH 6–8) and then the end-product is crystallized from a suitable solvent. According to a preferred embodiment, when a ($C_1$–$C_4$)alkyl ester of a ($C_1$–$C_4$) carboxylic acid is employed as the reaction solvent, in particular ethyl acetate, then the end-product may be crystallized directly from the same reaction solvent, without need of adding a different solvent for the crystallization.

For better illustrating the invention, the following examples are given.

EXAMPLE 1

Sequential growth of C. lunata and A. simplex

I) Slant Media
   Sabouraud medium (for *C. lunata*)
   Antibiotic Agar No. 1 (for *A. simplex*)
II) Vegetative and pre-culture media
   a) for *C. lunata*

| | |
|---|---|
| Soybean meal | 13 g/l |
| $KH_2PO_4$ | 5 g/l |
| Dextrose | 10 g/l |
| Peptone | 5 g/l | pH adjusted to 6.5–7.5 before autoclaving
   b) for *A. simplex*

| | |
|---|---|
| Dextrose | 1.0 g/l |
| Soybean meal | 5.0 g/l |
| Peptone | 5.0 g/l |
| Basamin Busch | 3.0 g/l |
| $KH_2PO_4$ | 5.0 g/l |
| NaCl | 5.0 g/l |
| Silicone | 0.1 ml/l | pH adjusted to 6.5–7.5 before autoclaving.
III) Fermentation media
   A fermentation medium having the same composition of the pre-culture medium for *C. lunata* reported above.
IV) Fermentation procedure
   The slants are used to separately inoculate 500 ml flasks which are cultured at about 28° C. for about 12–24 h (*C. lunata*) or 18–36 h (*A. simplex*) in the presence of 100 ml of the vegetative media indicated above. These inocula are used in the procedure described below:
   Aliquots (about 1 to 5%) of the culture of *C. lunata* obtained above are transferred in a 8 liter fermentor containing the above reported fermentation medium and cultivated for about 24 h at 29–32° C.

Then 4g of 2'-methyl-4-pregnen-21-ol-[17α,16α-d]-oxazolinyl-3,20-dione are added and the fermentation is continued until about 36–72 h from the inoculum.

Afterwards, the 18–36 h culture of *A. simplex* is added thereto and the fermentation is continued for further 40–55 h.

The reaction course is monitored as known in the art by TLC or preferably HPLC by following the disappearance of the starting material and/or appearance of the final product. As a further control, the appearance disappearance of intermediates can also be followed. HPLC conversion yield: 70–75%.

Recovery

After 40–55 h from the addition of *A. simplex* , the transformation can be generally considered as completed and the fermentation can be worked up to isolate the desired compound of formula I.

The fermentation mixture is separated by filtration, the mycelium is repeatedly washed with chloroform and the filtrate is extracted with chloroform (3×11). The combined chloroform washing and extracts are partially concentrated under reduced pressure and decolorized with charcoal. Then they are concentrated to an oily residue. On adding petroleum ether, a precipitate forms which is washed with ether 83 times) and collected by filtration giving 3 g of the compound of formula II.

EXAMPLE 2

Preparation of deflazacort

To a stirred solution of (11β,16β)-11,21-dihydroxy-2'-methyl-5'H-pregna-1,4-dieno[17,16-d]oxazole-3,20-dione (10 g, 0.025 mol) in 300 ml of ethyl acetate containing 4.5 g (0.25 mol) of water, 3.32 ml (0.035 mol) of acetic anhydride and 0.2 g (0.0016 mol) of 4-(N,N-dimethylamino) pyridine are added at a temperature of 5° C. The reaction is followed by TLC on silica gel using a mixture of chloroform/methanol 9/1 as eluent. After 6 hours, the reaction is considered completed.

EXAMPLE 3

Recovery of deflazacort

When the reaction of Example 1 is completed, the reaction mixture is allowed to reach room temperature and 85 ml of aqueous phosphate buffer solution (pH 7.5) are added thereto in 1 hour. The aqueous layer is discarded and the organic layer is washed with 80 ml of water, filtered and concentrated at about 30 ml. The crystalline suspension is kept at 5° C. for 2 hours; after filtration and drying, 10 g of crystalline product are obtained. By further concentrating the mother liquors at a volume of about 5 ml and cooling at 5° C., further 0.4 g of product are obtained, for a total of 10.4 g and an overall yield of 94% (purity >98%).

What is claimed is:
1. A process for preparing the compound (11β,16β)-21 (acetyloxy)-11-hydroxy-2'-methyl-5'H-pregna-1,4-dieno [17,16-d]oxazole-3,20-dione (deflazacort) of formula I

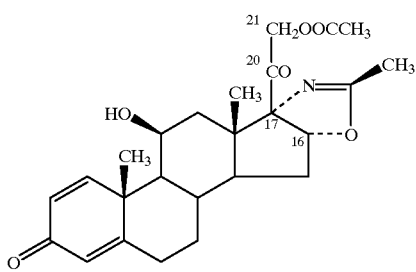

which comprises reacting (11β,16β)-11,21-dihydroxy-2'-methyl-5'H-pregna-1,4-dieno[17,16-d]oxazole-3,20-dione 20 of formula II

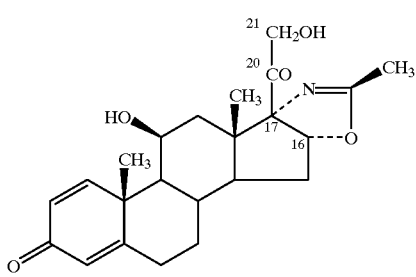

with acetic anhydride in a organic solvent, selected from halogenated ($C_1$–$C_4$)hydrocarbon, ($C_1$–$C_4$)alkyl ester of ($C_1$–$C_4$)carboxylic acid, dimethylformamide, acetonitrile and acetone, in the presence of a basic catalyst and water.

2. Process according to claim 1 wherein the organic solvent is a ($C_1$–$C_4$)alkyl ester of a ($C_1$–$C_4$)carboxylic acid.

3. Process according to claim 2 wherein the organic solvent is ethyl acetate.

4. Process according to claim 1 wherein the basic catalyst is selected from trimethylamine, triethylamine, N-methyl-pyrrolidine, pyridine, 4-(N,N-dimethylamino)pyridine, 4-(N,N-diethylamino)pyridine, collidine, picoline.

5. Process according to claim 1 wherein the reaction temperature is from −15° C. and 30° C.

6. Process according to claim 1 wherein the molar ratio between the compound of formula II and acetic anhydride is from 1.0:1.2 to 1.0:2.

7. Process according to claim 1 wherein the molar ratio between the compound of formula II and acetic anhydride is about 1.0:1.4.

8. Process according to claim 1 wherein the amount of basic catalyst is from 0.05 to 0.30 times the molar amount of the compound of formula II.

9. Process according to claim 1 wherein the amount of basic catalyst is from 0.05 to 0.10 times the molar amount of the compound of formula II.

10. Process according to claim 1 wherein the amount of water is from 3 to 20 times the molar amount of the compound of formula II.

11. Process according to claim 1 wherein the amount of water is from 5 to 15 times the molar amount of the compound of formula II.

12. Process according to claim 3 or 4 wherein deflazacort is recovered after completion of the reaction by washing the reaction mixture with an aqueous buffer solution at a pH of about 6–8, separating and filtering the organic phase and crystallizing the end-product from the same reaction solvent.

* * * * *